US00PP31992P3

(12) United States Plant Patent
Bourne

(10) Patent No.: US PP31,992 P3
(45) Date of Patent: Jul. 21, 2020

(54) GRAPEVINE PLANT NAMED 'SV22-88E-124'

(50) Latin Name: ***Vitis* spp.**
Varietal Denomination: SV22-88e-124

(71) Applicant: Sunview Vineyards of California, Inc., Delano, CA (US)

(72) Inventor: Timothy F Bourne, Visalia, CA (US)

( * ) Notice: Subject to any disclaimer, the term of this patent is extended or adjusted under 35 U.S.C. 154(b) by 0 days.

(21) Appl. No.: 16/501,069

(22) Filed: Feb. 14, 2019

(65) Prior Publication Data

US 2019/0335636 P1 Oct. 31, 2019

Related U.S. Application Data

(60) Provisional application No. 62/762,260, filed on Apr. 25, 2018.

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88; A01H 5/08
See application file for complete search history.

*Primary Examiner* — Keith O. Robinson
(74) *Attorney, Agent, or Firm* — Eric C. Cole; Baker Manock & Jensen, PC

(57) ABSTRACT

A new and distinct variety of grapevine plant named 'SV22-88e-124' particularly characterized by its amber colored berries with sweet, aromatic flavor similar to spun sugar. Additionally, berries of the new cultivar are very responsive to applications of exogenous gibberellic acid, producing looser clusters with larger berries compared to untreated clusters.

2 Drawing Sheets

Latin name of the genus and species of the plant claimed: The plant claimed relates to a new and distinct variety of *Vitis* spp.

Variety denomination: The plant claimed shall be known as 'SV22-88e-124'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis* spp. and hereinafter referred to as grapevine named 'SV22-88e-124'. As used herein, 'grapevine' refers to all plant parts including, vines, canes, tendrils, leaves, fruit and roots of 'SV22-88e-124'. Grapevine named 'SV22-88e-124' is the result of an effort to produce highly-flavored, crisp-textured grapes. This new cultivar originated from a cross conducted in May 2001 near McFarland, Calif. between seeded grapevine named '14-44-248' (U.S. Plant Pat. No. 14,923) and seedless, muscat-flavored grapevine 'Jupiter' (U.S. Plant Pat. No. 13,309). The resultant seeds were collected and stratified at 2° C. for three months and were planted in a greenhouse in a seedling flat. The seedlings from this effort were grown in the greenhouse at 29° C. with 12 hours illumination under high pressure sodium vapor lamps. The seedling population of 48 plants was planted in the field in the spring of 2002 near Delano, Calif. The new grapevine was selected from this seedling population on Jul. 20, 2006. It was then propagated by cuttings and grafted to 'Freedom'

(unpatented) rootstock in 2012. The present invention has been found to retain its distinctive characteristics through two successive asexual propagations.

Grapevine named 'SV22-88e-124' differs from the female parent grapevine '14-44-248' (U.S. Plant Pat. No. 14,923) in that 'SV22-88e-124' has elliptical shaped, seedless berries, whereas grapevine '14-44-248' (U.S. Plant Pat. No. 14,923) has ellipsoidal shaped, very large seeded berries which are reddish black in color.

Grapevine named 'SV22-88e-124' differs from its pollen parent, 'Jupiter' (U.S. Plant Pat. No. 13,309) by having amber colored, aromatic berries with a spun sugar flavor, while 'Jupiter' (U.S. Plant Pat. No. 13,309) has reddish black berries having a muscat flavor.

Grapevine named 'SV22-88e-124' differs from the commercial cultivar 'IFG Seven' (U.S. Plant Pat. No. 23,399) in that grapevine named 'SV22-88e-124' produces smaller amber colored berries whereas 'IFG Seven' (U.S. Plant Pat. No. 23,399) produces larger green colored berries. Additionally, the berry firmness of berries produced by grapevine named 'Sv22-88e-124' is crisp whereas the berry firmness of berries produced by 'IFG Seven' (U.S. Plant Pat. No. 23,399) is soft-medium.

SUMMARY OF THE INVENTION

The following are the most outstanding and distinguishing characteristics of this new variety when grown under normal horticultural practices near McFarland, Calif. Some of the characteristics may vary depending upon changes in crop load and change of location of cultivation.

1. Amber berry color;
2. Very crisp berry texture; and
3. Unusual flavor similar to spun sugar.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from a plant about 5 years-old, grown in a field near McFarland, Calif. in 2016.

DETAILED BOTANICAL DESCRIPTION

Figure 1:
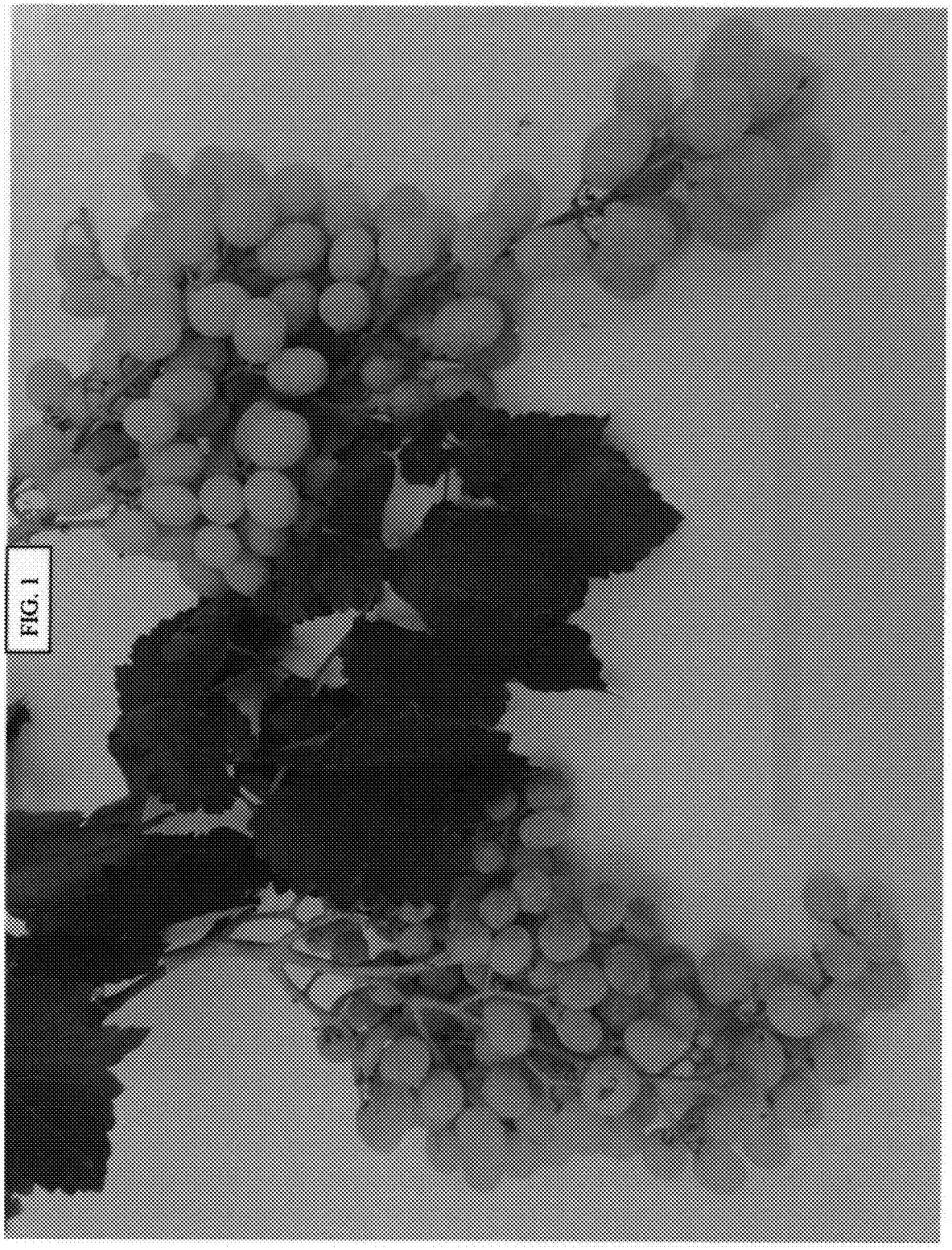
FIG. 1 Leaves and stems with natural fruit cluster on the left and fruit cluster from vine to which exogenous gibberellic acid was applied.
Figure 2:
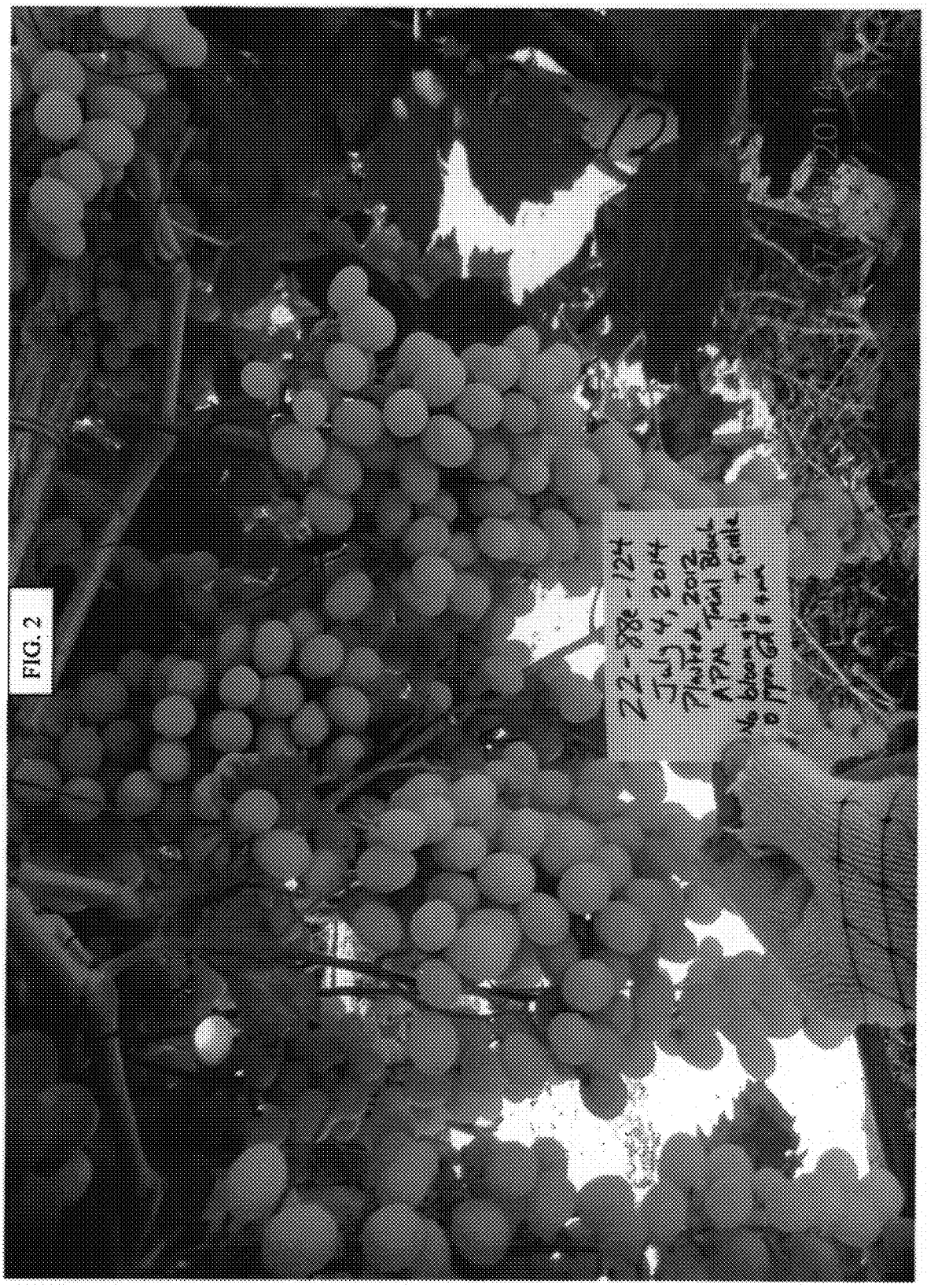
FIG. 2 Fruit on vine to which exogenous gibberellic acid was applied with vine girdling.

The following detailed description sets forth the distinctive characteristics of 'SV22-88e-124'. Descriptions of the new invention apply to vines of 'SV22-88e-124' grown on 'Freedom' rootstock at a density of 1,537 vines per hectare grown near McFarland, Calif. in 2017. These vines were in their fifth year of full production having been planted in 2012. These descriptions are believed to apply generally to the new variety grown under similar circumstances elsewhere. Variance from some of these traits may be expected depending upon cultural practices including fruit load as well season to season temperature variation. Color references are to The Royal Horticultural Society's Colour Chart, The Royal Horticultural Society, London, United Kingdom (1966, 1986, 1995, 2001.). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3)

Classification:

*Family*.—Vitaceae.
*Botanical name*.—*Vitis* spp.
*Variety name*.—'SV22-88e-124'.

Plant:

*Vigor*.—Medium.
*Density of foliage*.—Moderate.
*Productivity*.—Up to 43,000 kg/hectare.
*Hardiness*.—Hardiness observed to 0° C.
*Rootstock*.—'Freedom' (unpatented).

Trunk:

*Shape*.—Broadly elliptical.
*Straps*.—Split, from 22 cm. to 1 meter in length.
*Surface texture*.—Shaggy.
*Trunk circumference*.—24.3 cm.
*Inner bark color*.—Grey orange group 166D.
*Outer bark color*.—Brown group N200B.

Mature leaves:

*Average blade length*.—22.7 cm.
*Average blade width*.—18.2 cm.
*Size of blade*.—Large.
*Shape*.—Pentagonal.
*Number of lobes*.—3.
*Anthocyanin coloration of main veins on the upper side of the blade*.—None.
*Mature leaf profile*.—Variable with most leaves having margins cupped upwards while other leaves have a flattened profile.
*Blistering* (*upper surface*).—None.
*Leaf blade tip*.—Flat, within the plane of the blade.
*Margins*.—Lobed, serrated, mostly undulating.
*Apex*.—Narrowly acute.
*Bases*.—Sagittate.
*Thickness*.—Medium.
*Undulation of blade between main and lateral veins*.—Slight to pronounced.
*Shape of teeth*.—Broadly conical, both sides convex.
*Length of teeth*.—5-13 mm.
*Ratio length/width of teeth*.—About 0.8 to 1.0.
*General shape of petiole sinus*.—Half open.
*Tooth at petiole sinus*.—Absent.
*Petiole sinus limited by veins*.—Absent.
*Shape of upper lateral sinus*.—Variable, open to closed.
*Prostrate hairs between veins* (*lower surface*).—Absent.
*Erect hairs between veins* (*lower surface*).—Absent.
*Prostrate hairs on main veins* (*lower surface*).—Absent.
*Density of erect hairs on main veins* (*lower surface*).—Sparse. Limited to junction of main veins.
*Prostrate hairs on main veins* (*upper surface*).—Absent.
*Upper surface*.—Summer color: Green group 136A. Surface texture: Smooth. Surface appearance: Glossy. Goffering of blade: Absent.
*Lower surface*.—Summer color: Green group 137A. Anthocyanin coloration of main veins on lower leaf surface: Absent. Anthocyanin coloration on laterals: Absent. Glossiness: Dull. Pubescence: Absent. Surface texture: Rough. Surface appearance: Dull.
*Petiole*.—Length: 13.1 cm. Length of petiole compared to middle vein: Much shorter than main vein. Density of prostrate hairs: Absent. Density of erect hairs: Absent. Shape of base of petiole sinus: Broadly ovate to flattened conical. Color: In shade: Yellow green group 150B. In sun: Red purple group 60C.
*Buds*.—Time of bud burst: Early.

Tendrils:

*Number*.—Bifurcated and trifurcated; forming at and above node 6.
*Length*.—27.5 cm.
*Diameter*.—5.9 mm.
*Texture*.—Smooth.
*Color*.—In shade: Yellow green group 144D. In sun: Yellow green group 144D and red purple group 59B.

Growing tips (young shoot):

*Pubescence*.—Abundant, prostrate.
*Color*.—Yellow green group N144B.
*Anthocyanins*.—Slight.
*Shape*.—Flattened.
*Apex*.—Fully open.
*Shoot attitude*.—Semi-erect.

Flowers:

*Flower sex*.—Perfect.
*Position of first flowering nodes*.—Node 1 or node 2.
*Number of inflorescences per shoot*.—Generally 2 or 3.
*Date of full bloom*.—May 4, 2017.

Fruit:

*Ripening period*.—Mid-season.

*Date of ripening*.—August 10 at McFarland, Calif.

*Use*.—Fresh market.

*Keeping quality*.—Very good.

*Shipping quality*.—Good, some clusters have few berries with slight bruising.

*Date of first harvest*.—August 10.

*Solids-sugar*.—18 brix.

*Bunch*.—Size: Length (peduncle excluded): 27 cm. Width: 10.1 cm. Weight: Natural, without gibberellic acid treatment: 270 g. With gibberellic acid treatment: 606 g. Density: Loose. Number of berries: 110. Rachis color: In shade: Yellow green group N144D. In sun: Red purple group 61B (exposed portions of rachis only).

*Peduncle*.—Length: About 1.8 cm. Lignification: Slight, about 5 mm of length. Color: Yellow green group 144B.

*Berry*.—Uniformity of size: Variable. Weight Natural, without gibberellic acid treatment: 2.7 g. With gibberellic acid treatment: 5.8 g. Shape: Natural, without gibberellic acid treatment: Ellipsoidal. With gibberellic acid treatment: Ellipsoidal. Presence of seeds: Seedless; most berries develop one or two small, vestigial seeds about 3 mm in length, partially lignified. Cross section: Circular. Dimensions: Longitudinal axis: About 17.8 mm. Horizontal axis: About 16.8 mm. Skin color (without bloom): Yellow orange group 16C. Coloration of flesh: Translucent. Juiciness of flesh: Very juicy. Berry firmness: Crisp. Particular flavor: Sweet and aromatic. Bloom (cuticular wax): Heavy. Pedicel length: 7-10 mm. Berry separation from pedicel: Moderately difficult.

*Skin*.—Thickness: Thin. Texture: Tender. Reticulation: Absent. Roughness: Absent. Tenacity: Tenacious to flesh. Tendency to crack: Resistant.

Disease and insect resistance: No particular resistance or susceptibility has been observed. Normal disease control practices can be used.

Having thus described and illustrated our new variety of grapevine, We claim:

1. A new and distinct variety of grapevine plant named 'SV22-88e-124', substantially as illustrated and described herein.

* * * * *